United States Patent [19]

Bencini et al.

[11] Patent Number: 5,084,054

[45] Date of Patent: Jan. 28, 1992

[54] SURGICAL GRIPPING INSTRUMENT

[75] Inventors: Robert F. Bencini, Dracut; Berry D. Weitzner, Chelmsford; Stanley H. Remiszewski, Worcester, all of Mass.

[73] Assignee: C.R. Bard, Inc., Murray Hill, N.J.

[21] Appl. No.: 489,472

[22] Filed: Mar. 5, 1990

[51] Int. Cl.⁵ .............................................. A61B 10/00
[52] U.S. Cl. .................................. 606/113; 606/127; 606/206
[58] Field of Search ............... 606/110, 111, 113, 205, 606/206, 207, 208, 209, 127; 294/100

[56]  References Cited

U.S. PATENT DOCUMENTS

| 668,647 | 2/1901 | Jaenicke | 606/113 |
|---|---|---|---|
| 1,891,054 | 12/1932 | Pitman | 606/113 |
| 4,178,810 | 12/1979 | Takahashi . | |
| 4,461,280 | 7/1984 | Baumgartner . | |
| 4,467,802 | 8/1984 | Maslanka . | |
| 4,574,803 | 3/1986 | Storz . | |
| 4,656,999 | 4/1987 | Storz . | |
| 4,667,684 | 5/1987 | Leigh . | |
| 4,674,501 | 6/1987 | Greenberg . | |
| 4,815,476 | 3/1989 | Clossick . | |

FOREIGN PATENT DOCUMENTS 0027704  4/1981  European Pat. Off. ............ 606/113

Primary Examiner—Stephen C. Pellegrino
Assistant Examiner—Glenn K. Dawson
Attorney, Agent, or Firm—Darby & Darby

[57] ABSTRACT

A surgical gripping instrument comprises a support assembly, a slide mounted on the support assembly for relative movement with respect thereto, a wire movable with the slide relative to the support assembly, gripping means at the distal end of the wire, and a sheath enveloping the wire. Movement of the wire a predetermined distance relative to the sheath causes the gripping means to be actuated. A belt or gear arrangement is provided to enable the slide to be moved a distance relative to the support assembly less than the predetermined distance causing sufficient displacement of said sheath relative to the gripping means to actuate the latter.

11 Claims, 4 Drawing Sheets

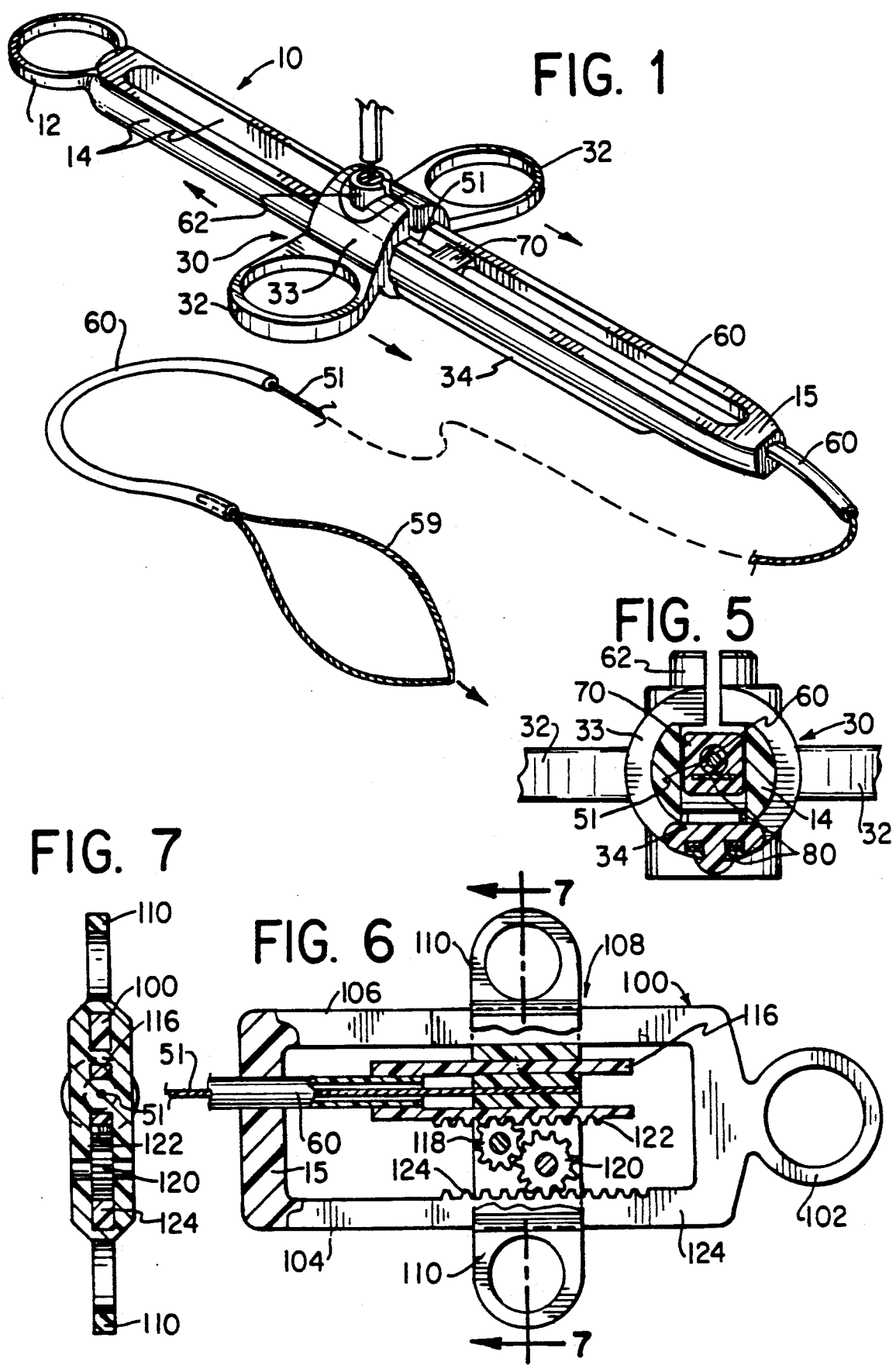

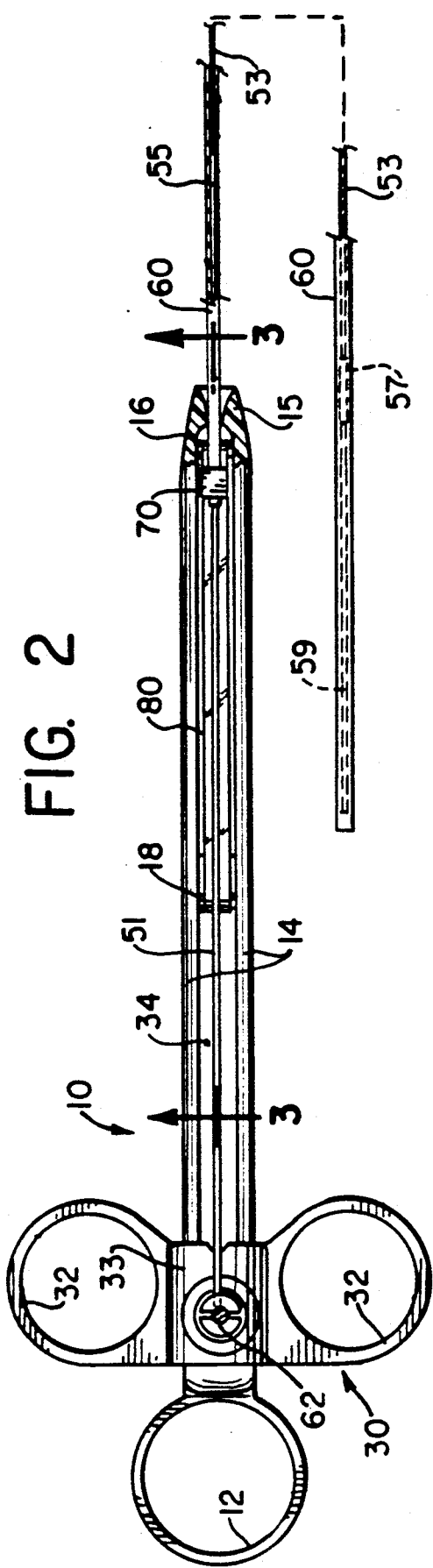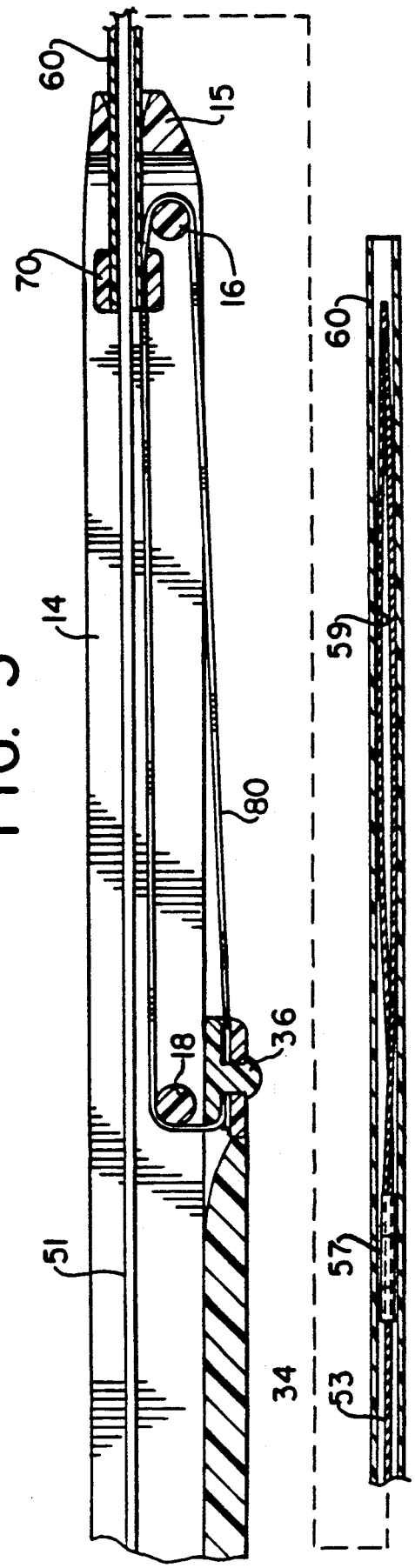

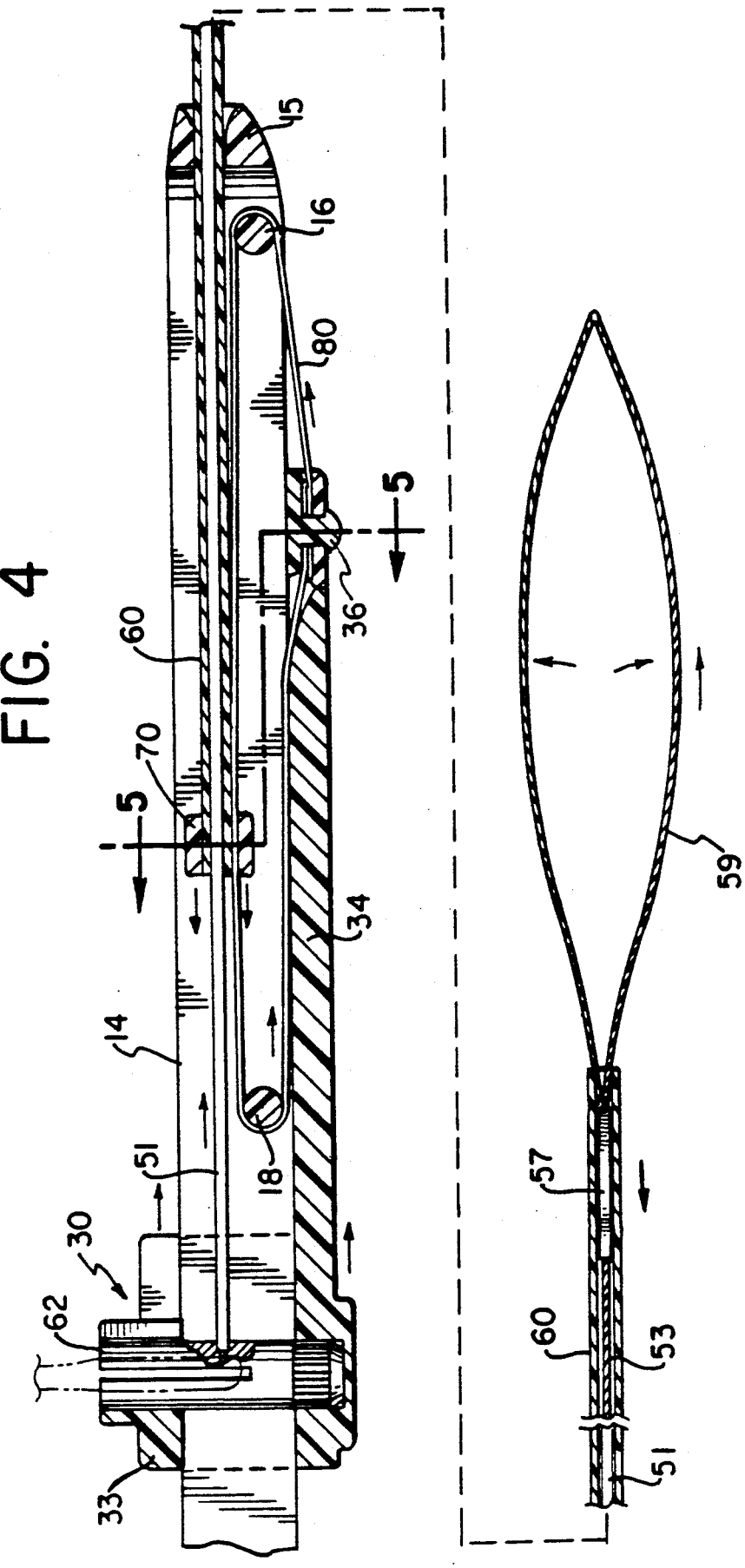

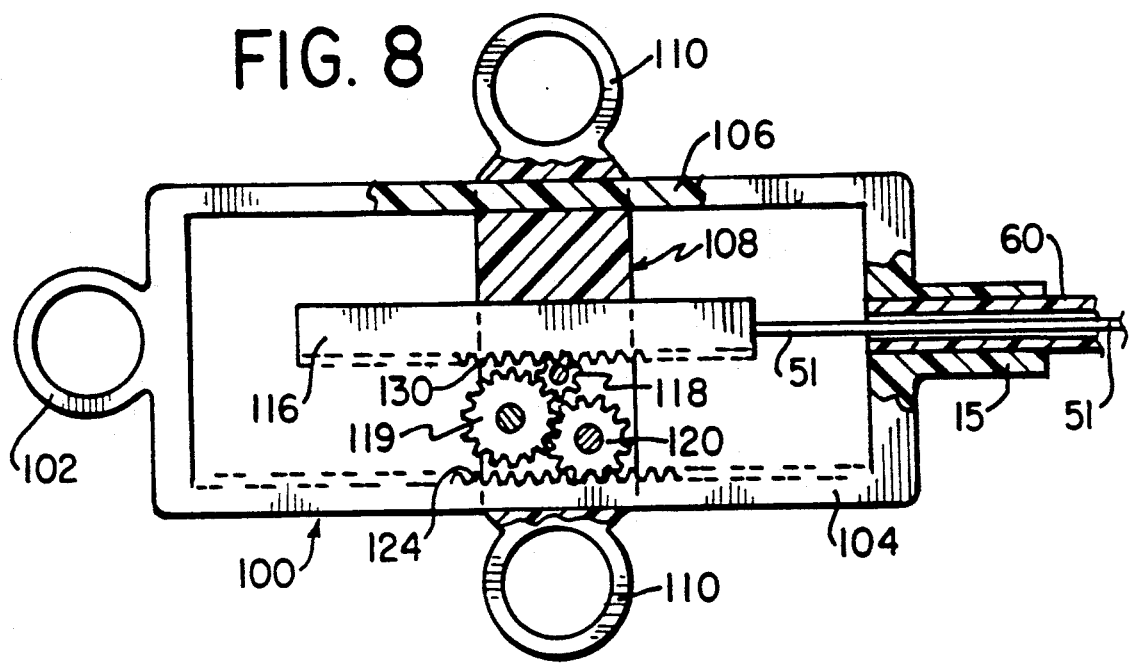
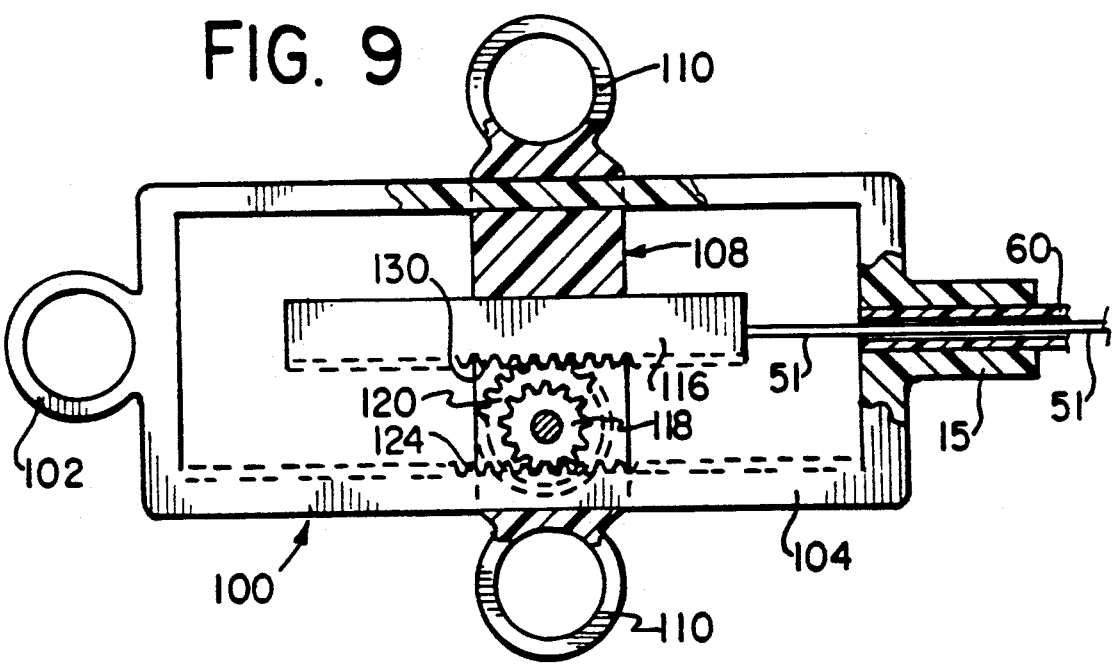

SURGICAL GRIPPING INSTRUMENT

This invention relates to surgical gripping instruments of the type which are introduced into body cavities and manually operated to grasp a portion of the patient's tissue.

BACKGROUND OF THE INVENTION

Manually operable surgical gripping instruments are well known. Typically, the gripping elements located at the distal end of the instrument are operated by movement of a wire or cable manipulated by the surgeon at the proximal end of the instrument. Very often, such instruments comprise a support assembly which includes a thumb hole and a slide which includes a finger grip and is movable with respect to the support assembly. The gripping instrument may be enclosed by a sheath such that when the wire pulls the gripping instrument into the sheath, the gripping instrument is actuated to grasp the tissue. Such gripping instruments are used for purposes such as bronchoscopy, bulboscopy, colonoscopy, duodenoscopy, endoscopy and gastroscopy.

In some situations, relatively substantial movement of the slide with respect to the support assembly is necessary to actuate the gripping instrument. For example, in the case of a polypectomy snare used to surgically remove polyps from the colon, it may be necessary to move the slide relative to the support assembly as much as three and a half inches. This movement, known as the "throw" of the instrument, is very often uncomfortable for the surgeon and sometimes two hands are needed to operate the device.

It is the principal object of this invention to provide a surgical gripping instrument of the type described wherein the throw required to actuate the instrument is reduced.

A further object of the invention is to provide a surgical gripping instrument which is cost efficient to manufacture as a disposable device and which is easier to use than comparable devices by virtue of the reduced throw required to actuate the gripping device.

A still more specific object of the invention is to provide a surgical gripping instrument of the type described which, while providing a reduced throw to actuate the gripping instrument, is similar in appearance and construction to known surgical instruments of this type.

SUMMARY OF THE INVENTION

Briefly, in accordance with the invention, a surgical instrument comprises a support assembly, a slide movable with respect to the support assembly, a sheath, and a wire passing through the sheath. Gripping means at the distal end of the wire are actuated when the wire is moved a predetermined distance relative to the sheath. In accordance with the invention, means are provided to increase the mechanical advantage of the device so that the displacement of the slide relative to the support assembly required to actuate the gripping device is substantially less than such predetermined distance.

In accordance with the illustrated embodiments, the actuating wire may be coupled to the slide and the sheath may be movable or it may be fixed to the support assembly. In the preferred embodiment, the sheath is movable and a belt secured to the sheath and slide causes the sheath to move in a direction opposite the direction of movement of the wire when the slide is moved. In other embodiments, gear means provide the desired mechanical advantage.

BRIEF DESCRIPTION OF THE DRAWINGS

The foregoing and other features of the present invention will be more readily apparent from the following detailed description of the drawings of illustrative embodiments of the invention in which:

FIG. 1 is a perspective view of a preferred embodiment of the invention showing the snare loop unsheathed;

FIG. 2 is a top view, partly in section, of the embodiment shown in FIG. 1 with the snare within the sheath;

FIG. 3 is an enlarged side sectional view along the line 3—3 of FIG. 2;

FIG. 4 is an enlarged side sectional view showing the snare unsheathed;

FIG. 5 is a sectional view along line 5—5 of FIG. 4;

FIG. 6 is a top view in section of a second embodiment of the invention;

FIG. 7 is a sectional view along line 7—7 in FIG. 6;

FIG. 8 is a top view in section of a third embodiment of the invention; and

FIG. 9 is a top view in section of a fourth embodiment of the invention.

DESCRIPTION OF THE PREFERRED EMBODIMENTS

As shown in FIG. 1, a surgical gripping instrument according to the invention has as a first component a support assembly 10 which includes a proximal thumb ring 12 and rails 14. Rails 14 are separated by a groove and connected at their proximal ends by thumb ring 12 and at their distal ends by an integrally formed front piece 15. Rails 14 are crescent-shaped in cross-section (FIG. 5). Distal and proximal axles 16 and 18 (FIG. 3) are transversely mounted in support assembly 10.

As a second component, a bifurcated slide 30 is slidably positioned on rails 14. Slide 30 comprises two finger rings 32, an annular body 33, and an elongated tongue 34 which extends beneath rails 14 (see FIG. 4). The interior of annular body 33 matches the cross-sectional area of rails 14 which thereby permits longitudinal movement of slide 30 relative to support assembly 10 between end cap 15 and thumb ring 12.

The third component is a wire assembly comprising rod 51, connector section 55 of rod 51 (FIG. 2) which connects rod 51 to a wire or cable 53, and connector 57 which connects wire 53 to a loop snare 59 at its distal end. Snare 59 is shown in FIG. 1 in an open or unsheathed position. A sheath 60 envelopes wire 53 and snare 59 except when wire 53 is in an extended position to open snare 59 into a loop as shown in FIGS. 1 and 4.

As shown in FIGS. 2-4, the proximal end of sheath 60 is secured to a block 70. Since block 70 is secured to sheath 60, longitudinal movement of block 70 between rails 14 will also cause the same longitudinal movement of sheath 60. Similarly, since rod 51 is secured to slide 30, longitudinal movement of slide 30 will cause the same movement of rod 51.

As shown in FIGS. 1 and 2, rod 51 extends through an aperture in front piece 15 and between the rails 14 through mounting block 70. Rod 51 is received within a bore (not numbered) in block 70 for axial movement with respect thereto. Rod 51 is not enclosed by sheath 60 and extends between rails 14 into annular body 33 where it is secured by connector 62. Connector 62 passes through so much of body 33 as needed to secure rod 51 within the slide 30. The internal diameter of sheath 60 is sized to enable rod 51, wire 53, snare 59 and connectors 55 and 57 substantially free longitudinal movement along its entire length.

FIG. 3 is an enlarged sectional view along lines 3—3 of FIG. 2 and shows a belt 80 which extends around the proximal axle 18, through block 70 in which it is securely fixed, and around distal axle 16. Tongue 34 which is a part of slide 30, extends from finger ring annular body 33 along the underside of rails 14 as shown in FIGS. 1 and 4. At the distal end of tongue 34 there is a heat seal pin 36 onto which is mounted the perforated ends of belt 80 as shown in FIG. 3. Belt 80 is thereby connected to slide 30 and is secured thereto by heating heat seal pin 36 to form a head as shown. Belt 80 may be fixed to block 70 (FIG. 3) by overmolding the block to the belt.

To operate the device shown in FIGS. 1-5, the user grasps the thumb ring 12 and finger holes 32 and pulls the slide 30 to the proximal end of the support assembly 10. In this position, the snare 59 is retracted within sheath 60 as shown in FIG. 3.

As is conventional, in one application of the invention, the surgeon inserts the distal end of the sheath 60 into the patient's colon until the polyp is located. Using one hand, the surgeon can then move the slide to the distal end of the support assembly which simultaneously causes the sheath 60 to be pulled toward the proximal end of the instrument and the wire assembly 51, 53 and 59 to be pushed toward the distal end of the instrument. This exposes and opens the snare 59 so that it can be used to snare the patient's polyp. If, for example, three inches of movement of the gripping means relative to the sheath are required to fully unsheath the snare 59, with the surgical instrument shown in FIGS. 1-5, it is only necessary for the surgeon to move the slide 1.5 inches relative to the support assembly.

When the snare has been positioned around the polyp to be removed, the surgeon then pulls the slide back toward the distal end of the support assembly. This causes the slide to pull the wire assembly and snare 59 toward the proximal end of the instrument while at the same time the sheath 60 is pushed toward the distal end causing the snare to close around the polyp. Again, the movement of the slide relative to the support assembly necessary to cause the snare to be retracted is one-half the movement of the snare relative to the sheath. Hence, even if displacement of the snare relative to the sheath is in the order of four inches, the surgeon need move the slide relative to the support assembly only two inches which is a relatively simple matter.

Although the preferred embodiment of the present invention has been described as a snare, the principles of the invention are applicable to other surgical gripping devices such as grasping forceps, biopsy forceps, retrieval baskets, mechanical lithotriptors, etc. Furthermore, remote electrostimulation, cauterization, or other electromechanical operations or procedures can be accomplished at the gripping end of the device if the sheath is made of an electrical insulating material, the wire cable, rod, and electrical connector 62 are made of electrical conductive materials, and an external electrical connector of a power source, an instrument or a measuring device is attached to connector 62 (FIG. 1).

FIGS. 6 and 7, 8 and 9 shows three additional embodiments of the invention in which gears are used to provide the mechanical advantage for reducing the throw of the device. With respect to these embodiments, the devices are shown schematically. In each case, as in the case of the embodiment of FIGS. 1-5, the rod which is attached to the snare or other gripping means is shown at 51 and the sheath at 60. The support assembly is shown at 100 terminating in a thumb ring 102. The support assembly 100 includes two rails 104 and 106 on which a slide 108 is adapted to move longitudinally (axially). The slide includes finger rings 110 so that the user can move the slide 108 relative to the support assembly 100 by grasping in one hand the finger holes 110 and the thumb hole 102.

In the embodiment shown in FIGS. 6 and 7, the wire rod 51 is secured to the slide 108 and moves with it. A cap 116 is secured to the sheath 60 and arranged for axial, slidable movement with respect to the slide 108. Two pinions 118 and 120 are rotatably supported within the slide 108 (see FIG. 7) and engage, respectively, rack 122 on the sheath cap 116 and rack 124 on the upper surface of rail 104.

Depending on the diameters of the pinions 118 and 120, as the slide 108 is moved relative to the support assembly 100, the wire is moved in one direction and the sheath in the other direction. As one example, the sizes of the pinions 118 and 120 may be selected so that the relative displacement of the slide to the support assembly is one half that of the sheath 60 relative to the rod (and snare) 51. In the embodiment of FIGS. 6 and 7, as the slide is pulled proximally toward the thumb ring 102, the wire 51 is pulled in the same direction causing it to be retracted into the sheath. Simultaneously, this proximal movement of slide 108 rotates pinion 120 clockwise causing pinion 118 to rotate counterclockwise and the cap 116 to move in a distal direction, thereby advancing the sheath around the retracting snare (with respect to the support assembly 100). As the slide 108 is advanced toward the distal end (to the left in FIG. 6), pinion 120 rotates counterclockwise causing pinion 118 to rotate clockwise which drives sheath 60 to the right. At the same time, the wire 51 which is secured to the slide is moved distally (to the left).

In the embodiment of FIG. 8, a third pinion 119 is mounted on the slide 108 in engagement with the pinions 118 and 120. Pinion 118 engage a rack 130 on cap 116. Moreover, the sheath 60 is immovably secured to the distal end of the support assembly 100 so that, in this case, only the wire is movable. Because of the addition of the third gear, in the embodiment of FIG. 8, the mounting cap 116 and the rod 51 move in the same direction as the movement of the slide 108 relative to the support assembly 100. In other words, if the user pulls the finger grip 110 towards the thumb hole 102, the three pinions 118, 119 and 120 also pull the rod 51 towards the thumb hole, i.e., towards the support assembly 100 which tends to pull the snare into the sheath 60. In this embodiment, as the slide 108 is advanced distally (to the right in FIG. 8) pinion 120 rotates clockwise, pinion 119 rotates counterclockwise, and pinion 118 rotates clockwise thus moving rack 116 and the wire 51 also in the distal direction (to the right). In other words, the wire moves in the direction of movement of the slide at a different rate.

FIG. 9 is similar to FIG. 8 in that the sheath 60 is immovably secured to the support assembly 100 but in this case the pinions 118 and 120 are coaxially mounted, with pinion 118 engaging rack 124 and pinion 120 engaging rack 130. Movement of the slide 108 distally (to the right) rotates both pinions 118 and 120 clockwise which again moves rack 116 in the distal direction (to the right), i.e., in the same direction of movement as the slide.

In the embodiments of FIGS. 8 and 9, as in the case of the embodiment of FIGS. 6 and 7, the relative size of the pinions determines the mechanical advantage of the instrument, i.e., the throw required to actuate the gripping device. It is contemplated that with the embodiments of FIGS. 8 and 9, a mechanical advantage as high as four may be obtained, i.e., the throw required to actuate the gripping device will be one-fourth the actual movement of the gripping device relative to the sheath.

A surgical instrument in accordance with the invention may be made of any suitable material. It is contemplated that the device itself can be made disposable in which case both the support assembly 10 and the slide will be molded from a suitable plastic such as polycarbonate or other inert plastic.

What is claimed is:

1. In a surgical gripping instrument of the type including a sheath, gripping means at the distal end of said sheath movable with respect to said sheath a predetermined distance for actuating said gripping means, a support assembly, and a slide movable with respect to said support assembly, said slide being connected to at least one of said sheath and said gripping means for movement thereof, the improvement comprising means responsive to movement of said slide relative to said support assembly a distance less than said predetermined distance for causing said gripping means to be moved relative to said sheath said predetermined distance in order to actuate said gripping means.

2. A surgical instrument according to claim 1, wherein said means responsive comprises means for simultaneously moving said gripping means in one direction and said sheath in the opposite direction.

3. A surgical instrument according to claim 2, wherein said means responsive comprises means connecting said slide to said gripping means and a belt connected to said sheath and slide.

4. A surgical instrument according to claim 1, wherein said means responsive comprises rotatable gears mounted on said slide and engaging said sheath or said gripping means.

5. A surgical gripping instrument, comprising:
a support assembly;
a slide mounted on said support assembly for relative movement with respect thereto;
a wire movable with said slide relative to said support assembly;
gripping means at the distal end of said wire;
a sheath enveloping said wire, movement of said wire a predetermined distance relative to said sheath causing the gripping means to be actuated; and
enabling said slide to be moved a distance relative to said support assembly less than said predetermined distance to actuate said gripping means.

6. A surgical gripping instrument according to claim 5, wherein said sheath is movable relative to said support assembly, and wherein said means enabling comprises means for moving said wire in one direction and simultaneously moving said sheath in the opposite direction.

7. A surgical gripping instrument according to claim 6, wherein said wire is secured to said slide, wherein said support assembly includes distal and proximal axles and wherein said means enabling comprises a belt fixed at both ends to said slide, said belt passing over both of said axles and secured to said sheath, whereby movement of said slide in one direction causes rotation of said belt and movement of said sheath in the opposite direction.

8. A surgical gripping instrument according to claim 5, wherein said sheath is movable relative to said support assembly and wherein said means enabling comprises gear means connected to said sheath and support assembly for moving said sheath in a direction opposite the direction of movement of the slide relative to the support assembly.

9. A surgical gripping instrument according to claim 5, wherein said sheath is fixed to said support assembly, wherein said wire is movable relative to said slide, and wherein said enabling means comprises gear means for moving the wire a distance relative to the support assembly greater than the displacement of the slide relative to said support assembly as the slide is moved.

10. A surgical gripping instrument according to claim 9, wherein said gear means causes said wire to move in a direction opposite the direction of movement of the slide relative to the support assembly.

11. A surgical gripping instrument according to claim 9, wherein said gear means causes said wire to move in the same direction as the slide relative to the support assembly.

* * * * *

UNITED STATES PATENT AND TRADEMARK OFFICE
CERTIFICATE OF CORRECTION

PATENT NO. : 5,084,054

DATED : January 28, 1992

INVENTOR(S) : Robert F. Bencini et al.

It is certified that error appears in the above-identified patent and that said Letters Patent is hereby corrected as shown below:

On the cover page of the patent, at paragraph "[75] Inventors:", please delete "Berry D. Weitzner," and substitute therefor --Barry D. Weitzner,--.

Signed and Sealed this

Fifth Day of January, 1993

Attest:

DOUGLAS B. COMER

*Attesting Officer*      Acting Commissioner of Patents and Trademarks